US009333107B2

(12) United States Patent
Potter et al.

(10) Patent No.: US 9,333,107 B2
(45) Date of Patent: May 10, 2016

(54) BRACE SYSTEM

(71) Applicant: Boston Dynamics, Inc., Waltham, MA (US)

(72) Inventors: Steven D. Potter, Bedford, MA (US); Christopher Everett Thorne, Somerville, MA (US); Michael Patrick Murphy, Waltham, MA (US)

(73) Assignee: Google Inc., Mountain View, CA (US)

( * ) Notice: Subject to any disclaimer, the term of this patent is extended or adjusted under 35 U.S.C. 154(b) by 230 days.

(21) Appl. No.: 13/967,541

(22) Filed: Aug. 15, 2013

(65) Prior Publication Data

US 2015/0051527 A1 Feb. 19, 2015

(51) Int. Cl.
 | | |
 |---|---|
 | A61F 5/00 | (2006.01) |
 | A61F 5/01 | (2006.01) |
 | A61H 1/02 | (2006.01) |
 | A61H 3/00 | (2006.01) |

(52) U.S. Cl.
CPC .............. *A61F 5/0125* (2013.01); *A61H 1/024* (2013.01); *A61H 3/00* (2013.01); *A61F 2005/0137* (2013.01); *A61F 2005/0139* (2013.01); *A61F 2005/0144* (2013.01); *A61F 2005/0169* (2013.01); *A61H 2201/1246* (2013.01); *A61H 2201/149* (2013.01); *A61H 2201/165* (2013.01); *A61H 2201/1642* (2013.01); *A61H 2201/5061* (2013.01); *A61H 2201/5071* (2013.01); *A61H 2201/5084* (2013.01)

(58) Field of Classification Search
CPC ................ A61H 2201/1642; A61H 2201/165; A61H 3/008; A61H 2201/1215; A61H 2201/5061; A61H 3/00; A61H 2201/1676; A61H 1/0237; A61H 1/024; A61H 1/0266; A61H 1/0274; A61H 2201/123; A61H 2201/50; A43B 13/182; A43B 13/184; A61F 5/0125
USPC ...................... 602/16, 23–28; 128/882; 5/624
See application file for complete search history.

(56) References Cited

U.S. PATENT DOCUMENTS

| | | | |
|---|---|---|---|
| 3,969,773 A | 7/1976 | Menschik | |
| 3,976,057 A | 8/1976 | Barclay | |
| 4,372,298 A | 2/1983 | Lerman | |
| 4,773,404 A | 9/1988 | Townsend | |
| 5,204,104 A | 4/1993 | Bolinger et al. | |
| 5,213,094 A * | 5/1993 | Bonutti | ........................ 601/33 |
| 5,472,412 A | 12/1995 | Knoth | |
| 5,662,693 A * | 9/1997 | Johnson et al. | ................. 607/49 |
| 6,080,123 A | 6/2000 | Pansiera | |
| 6,971,996 B2 | 12/2005 | Houser | |

(Continued)

OTHER PUBLICATIONS

Pratt et al., "The RoboKnee: An Exoskeleton for Enhancing Strength and Endurance During Walking", IEEE 2004, pp. 2430-2435.

(Continued)

*Primary Examiner* — Michael Brown
(74) *Attorney, Agent, or Firm* — McDonnell Boehnen Hulbert & Berghoff LLP

(57) ABSTRACT

A brace system includes a medial brace and a lateral brace securable via cross members. Each brace has an upper portion, a lower portion, and a hinge assembly between the upper and lower portion configured to allow translation of the lower portion relative to the upper portion.

23 Claims, 21 Drawing Sheets

(56) References Cited

U.S. PATENT DOCUMENTS

| | | |
|---|---|---|
| 6,981,957 B2 | 1/2006 | Knecht et al. |
| 7,507,215 B2 | 3/2009 | Ryan |
| 2004/0225245 A1 | 11/2004 | Nelson |
| 2008/0287850 A1* | 11/2008 | Adarraga ................. 602/26 |
| 2013/0038056 A1 | 2/2013 | Donelan et al. |
| 2013/0245524 A1* | 9/2013 | Schofield ................ 602/16 |

OTHER PUBLICATIONS

Grant A. Elliott, "Design and Evaluation of a Quasi-Passive Robotic Knee Brace: On the Effects of Parallel Elasticity on Human Running", Ph.D. Thesis, M.I.T., Dept. of Electrical Engineering and Computer Science, 2012, 139 pages.

* cited by examiner

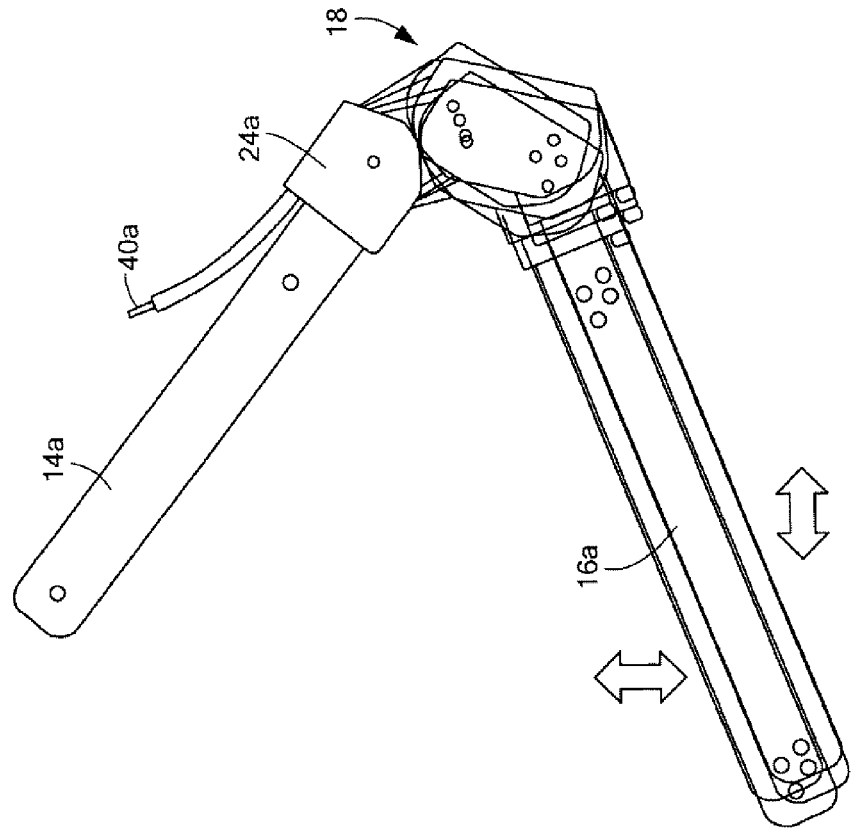
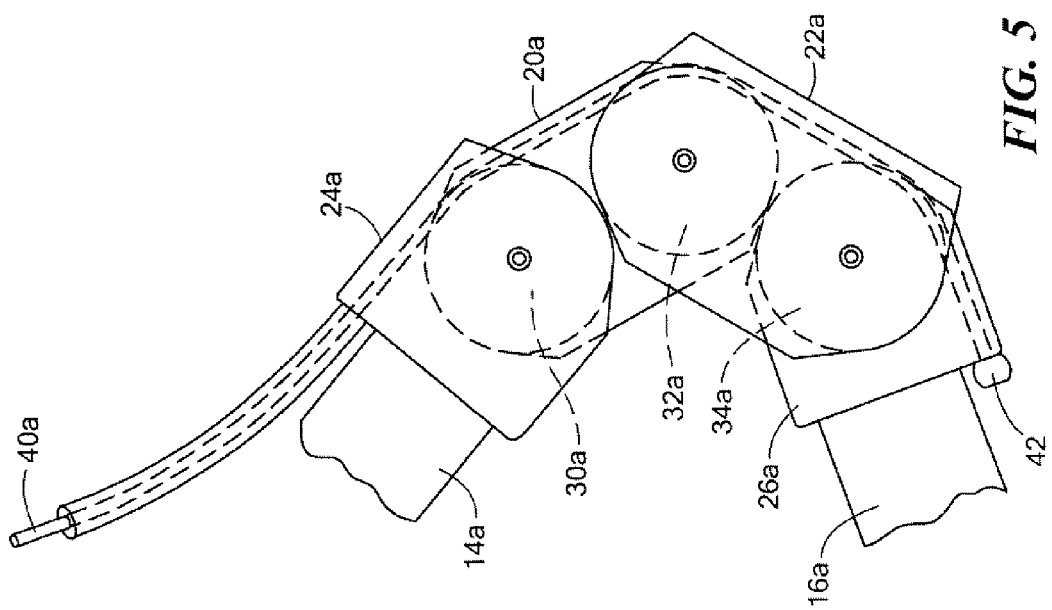

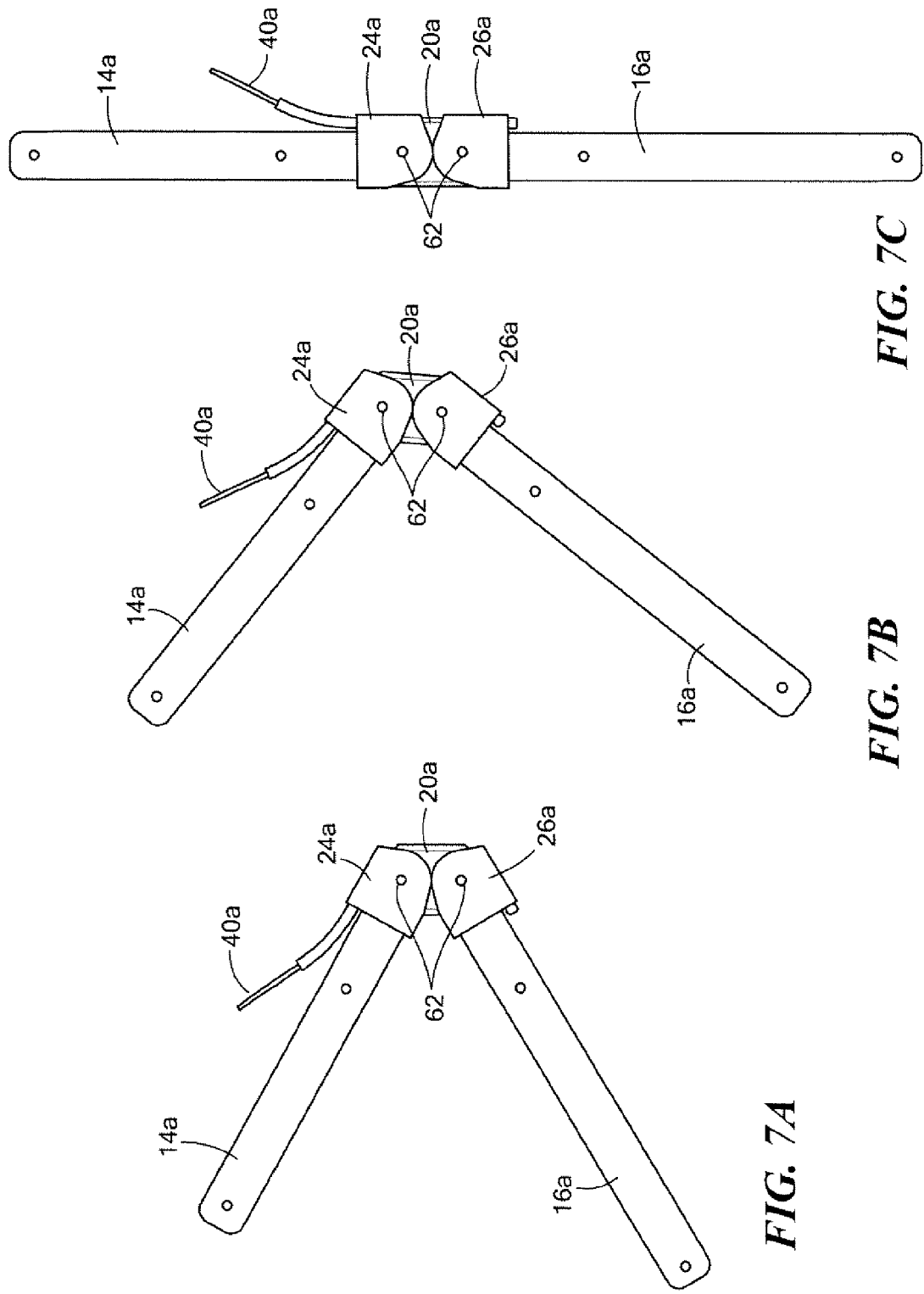

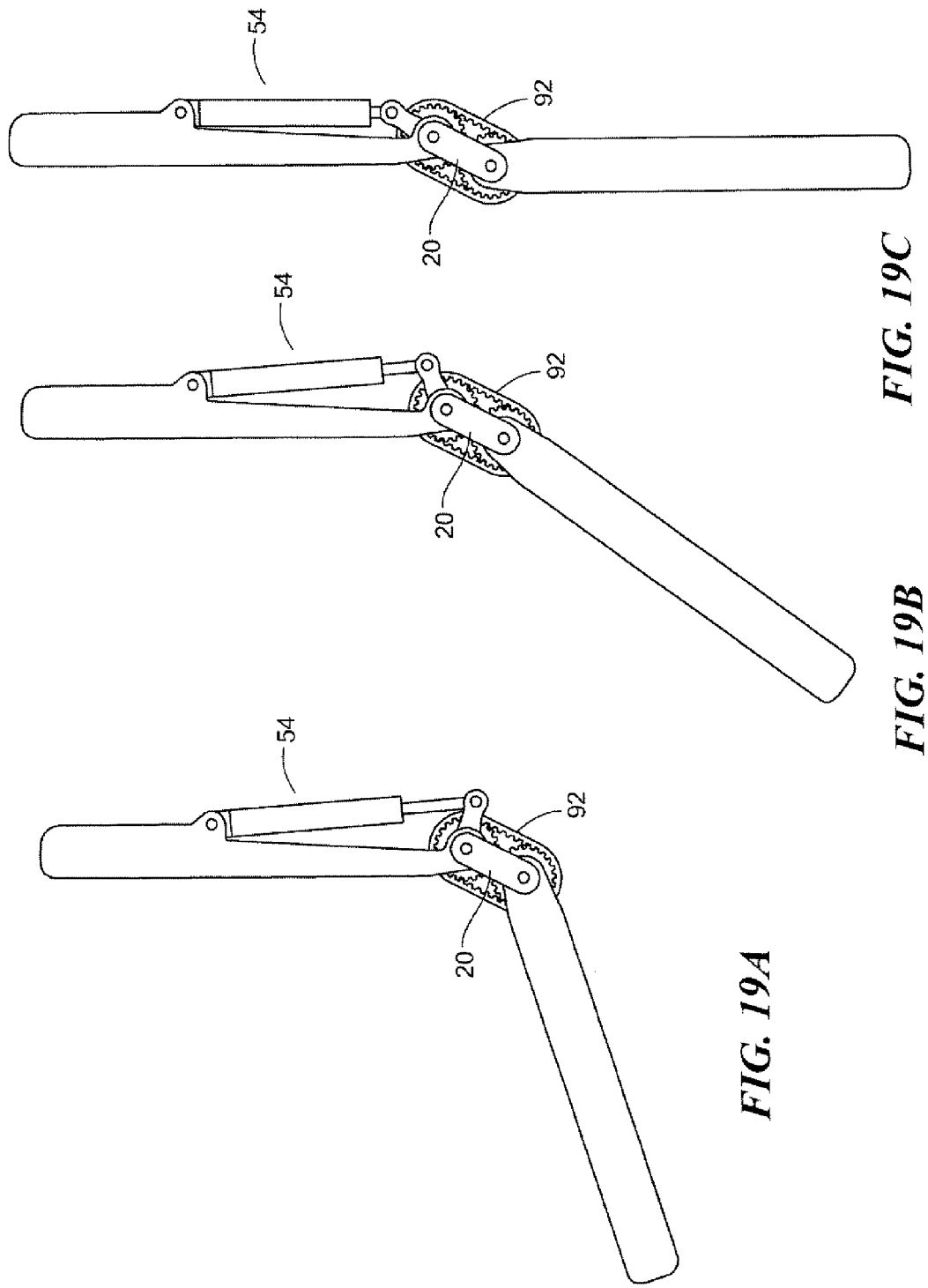

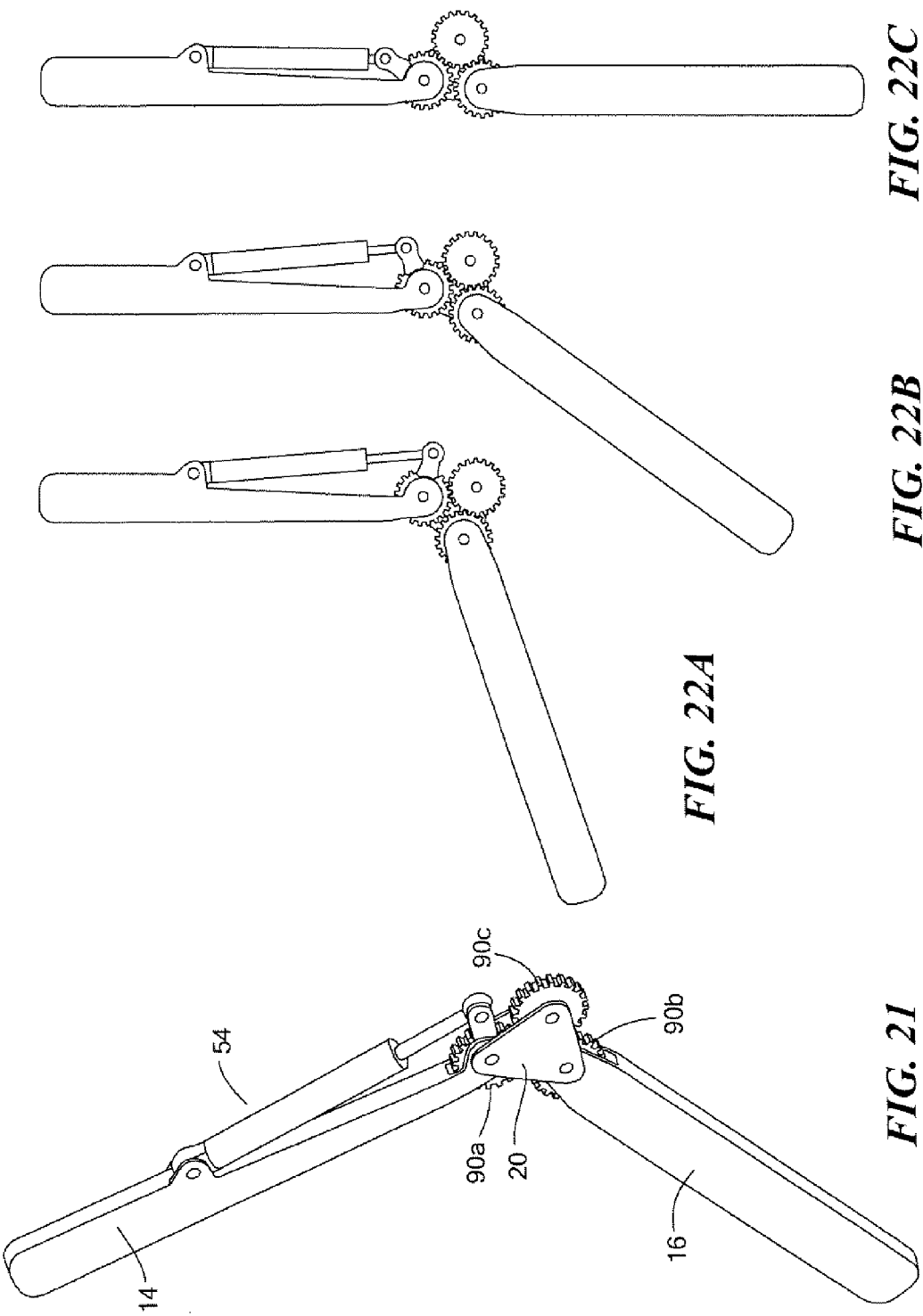

BRACE SYSTEM

GOVERNMENT RIGHTS

This invention was made with U.S. Government support under Contract No. W911QX-12-C-0085 awarded by DARPA. The Government may have certain rights with regard to the invention.

FIELD OF THE INVENTION

The present invention relates to orthotics and exoskeletons. Aspects of the invention relate to braces which can assist the flexion or extension of a joint, e.g., the knee joint.

BACKGROUND OF THE INVENTION

Knee braces are varied in design. Most have one component strapped to the thigh and another component strapped to the calf with a pivotable link therebetween. See U.S. Pat. No. 4,372,298 incorporated herein by this reference.

Other designs have a damper between two pivoting components and even sensors for controlling the damper. See U.S. Pat. No. 7,507,215 incorporated herein by this reference.

Many knee braces are designed with rehabilitation in mind. Typically, natural knee joint motion is inhibited or constrained in some way.

There is a different need, however, for new knee and other joint braces which can be used for other purposes. In one example, a soldier wearing a pack might benefit from a knee brace which not only provides stability but also reduces the load on the muscles of the knee, particularly the quadriceps. Indeed, when the knee bends, it would be beneficial to lower the load carried by the knee. Energy stored during the bending action can be used to straighten the knee. When the leg swings forward for the next step, it would be advantageous if the knee brace freely operated.

Most exoskeletons to date have been designed to off-load the weight of a backpack or other payload using a parallel load path of structural limbs, joints and actuators. These devices are often heavy, bulky and awkward to use.

A lighter and less-restrictive approach is to use a brace to apply torque to the limbs adjacent to a joint to assist the flexion or extension of the joint. This reduces muscle fatigue as well as reducing the skeletal forces needed to react the muscle forces. This type of assistive brace is relatively rare.

Most orthotic braces are designed to stabilize an injured joint, not apply torque. In general, the goal is to approximate the motion of the joint while protecting it from side loads and twisting.

To date, most assistive braces are adaptations of orthotic braces. As a consequence, these devices are needlessly heavy, bulky and restricting, and they typically require custom-fitting to each user.

Key research examples of assistive knee braces are as follows and incorporated herein by this reference:

Ryan U.S. Pat. No. 7,507,215 describes a knee brace with an X-style polycentric hinge, rigid upper and lower leg cuffs, and adjustable hydraulic damping.

Donelan et al, US 2013/0038056 A1 describes a knee brace with a simple hinge joint and rigid upper and lower shells. The brace is coupled to a generator that charges batteries only when the knee is doing negative work.

Grant Elliot's PhD thesis, MIT 2012, describes a knee brace with a clutchable spring. His brace uses rigid upper and lower arms and a gear-style one degree of freedom (DOF) polycentric hinge.

Yobotics Inc.'s RoboKnee uses an electric series-elastic actuator to drive a knee brace with a geared 1-DOF polycentric joint and rigid upper and lower arms.

See also U.S. Pat. Nos. 6,971,996; 5,472,412; 3,976,057; 6,080,123; 6,981,957; 3,969,773 and US 2004/0225245 all incorporated herein by this reference.

Most braces use 1-DOF hinges and are thus very sensitive to alignment of the brace to the knee joint. This problem is much worse for assistive (torque-producing) braces. Mismatch between the instantaneous center of rotation of the hinge and of the knee causes uncomfortable or dangerous loads on the knee as well as making the brace migrate down the leg. The mismatch is inevitable because the 1-DOF hinges are only an approximation of the motion of the knee and because of deflection of the flesh where the brace attaches to the leg.

A second disadvantage with the most braces is that they require rigid structure spanning between the medial and lateral hinges. This enforces a fixed width and makes the brace wider than necessary since it must accommodate the width of the knee at the desired maximum flexion position. To avoid a sloppy fit and interference of the braces of the left and right legs, these braces will typically require custom fitting to each user.

A third disadvantage is that most prior art braces do not allow twisting of the foreleg and thus restrict a normal DOF of the leg. This makes the braces awkward to use and increases the likelihood of chafing and migration of the brace. Some knee braces are complex, difficult and expensive to mass produce, and uncomfortable to use in daily activities.

SUMMARY OF THE INVENTION

One brace system in accordance with the invention applies flexion or extension torque to a joint while allowing the normal motion of the joint. For instance, to assist the knee joint, a pure torque is applied to the thigh and an equal and opposite torque is applied to the foreleg. Properly applied, these torques cancel out and avoid shear forces on the joint.

Brace systems in accordance with examples of the invention allow a twist DOF (e.g., a knee brace that allows twisting of the foreleg), are relatively insensitive to alignment, and are lightweight, low-profile, and fit people (or animals) of various sizes. In one aspect, the brace straps can be mostly made of soft materials and can be integrated into clothing or worn under clothing. The medial and lateral braces can taper inwardly to follow the contour of the joint.

Featured is a brace comprising an upper arm, a lower arm, and a hinge assembly. The upper and lower arms attach to the upper and lower limbs of a human or animal joint and are connected by a hinge assembly. An actuator coupled to the hinge assembly produces torque urging flexion or extension of the arm assembly.

Also disclosed are two features which can be utilized separately or preferably in combination. The first feature is a hinge assembly with at least one, and preferably at least two intermediate links pivotably connected in series between the upper and lower arms. The link(s) provide at least one redundant DOF allowing flexion/extension of the brace. The hinge assembly may also includes a parallel-action mechanism that allows the lower arm to translate substantially freely in at least one DOF relative to the upper arm, even when the brace is under load.

Using one intermediate link provides one under-actuated, translational DOF. This makes the brace relatively insensitive to vertical alignment, e.g. the vertical position of the hinge assembly relative to the knee. The redundant DOF also accommodates the polycentric motion of a joint which can, for example, allow a deeper knee bend.

The use of two or more intermediate links allows planar/parallel motion of the lower arm relative to the upper arm. This makes the brace less sensitive to fore-aft misalignment. In effect, the hinge assembly can stretch and contract in the longitudinal direction. With many intermediate links, it is possible to drive the joint with a single hinge assembly located anterior or posterior to the joint.

The parallel action mechanism can be achieved, for example, using tendons and pulleys, parallelogram linkages, gears or combinations thereof. The actuator produces torque in the flexion/extension direction for example by pulling on a tendon or by driving one of the pulleys, gears or linkages. Some embodiments allow torque to be applied only in one direction, e.g. to extend the knee. Other embodiments allow bi-directional torque.

A second enabling feature is the use of a force differential between brace assemblies located on the medial and lateral sides of a joint. This allows the actuator (or actuators) to apply equal torque to the two brace assemblies, but does not require them to move in tandem. The result is an additional non-actuated DOF of the brace: the ability to twist. In the knee brace example, this DOF allows medial/lateral rotation of the ankle relative to the knee. Note that the body uses the same principle to allow twisting of the foreleg or forearm. This is why we have two bones in our forelimbs.

Driving both brace assemblies removes the need for any rigid structures connecting between the medial and lateral arms. This reduces the size and weight of the brace and allows for width adjustment using straps. An additional advantage is that the hinge assemblies on the medial and lateral sides do not have to be parallel (as viewed from the front). Since people's legs and knees are generally tapered, this allows the hinge assemblies to lie closer to the knee which reduces the likelihood of interference with the brace on the opposite leg.

The force differential can be implemented, for example, using an actuator to drive a pulley that pulls on two tendons, one going to each of the brace assemblies. In another example, the brace assemblies are driven by separate hydraulic actuators connected by a differential hydraulic circuit, e.g. connected by a conduit.

Featured is a brace system comprising a medial brace and a lateral brace securable via cross members. Each brace includes an upper portion, a lower portion, and a hinge assembly between the upper and lower portion including at least tow intermediate links configured to allow translation of the lower portion relative to the upper portion. A force differential actuator subsystem is connected to the medial and lateral braces.

In one example, each hinge assembly includes a tendon. Each hinge assembly may include a parallelogram linkage. The force differential actuator subsystem may include a hydraulic actuator coupled to the tendons. In another version, the force differential actuator subsystem includes an actuator for each brace coupled to a differential hydraulic circuit.

Also featured is a brace system comprising a medial brace and a lateral brace securable via cross members. Each brace includes an upper portion, a lower portion, and a hinge assembly between the upper and lower portions including a mechanical parallel action mechanism with at least one intermediate link.

The brace system may further include a force differential actuator subsystem connected to the hinge assemblies. The cross members are preferably pliable allowing the medial and lateral braces to taper inwardly to more closely conform to a joint. Each brace upper and lower portions are preferably pivotably connected by two or more intermediate links pivotably connected in series in the hinge assembly. In one design, each hinge assembly is configured with at least one non-actuated degree of freedom allowing translation of the lower portion with respect to the upper portion. The force differential actuator subsystem may include a tendon for each hinge assembly and at least one actuator. In one version, the tendons for each hinge assembly are interconnected and differentially coupled to an actuator. In another embodiment, the force differential actuator subsystem includes an actuator for each brace coupled to a differential hydraulic circuit. In some designs, the hinge assembly includes a plurality of serially connected pivoting links coupled together by at least a pulley wheel section rotatably coupled between adjacent links.

Also featured is a brace comprising an upper portion, a lower portion, a mechanical parallel action hinge assembly pivotably coupling the upper and lower portions including at least one intermediate link, and an actuator subsystem configured to apply substantially equal and opposite torque to the upper portion and lower portion while allowing substantially free translation of the lower portion with respect to the upper portion.

In one version, the mechanical parallel action hinge assembly includes at least sections of pulley wheels associated with the intermediate link and a tendon over the pulley wheel sections coupled to an actuator. The parallel action mechanism may include a four bar linkage with at least one link driven by an actuator. The parallel action mechanism may include gears associated with the intermediate link at least one of which is driven by an actuator. The brace may have at least two serially connected intermediate links.

One brace featured includes an upper portion, a lower portion, a hinge assembly pivotably coupling the upper and lower portions including at least two serially connected intermediate links, and a torque actuator subsystem configured to apply substantially equal and opposite torque to the upper portion and lower portion while allowing substantially free translation of the lower portion in two planar degrees of freedom with respect to the upper portion.

Also featured is a brace system for a joint comprising a medial brace and a lateral brace securable via flexible cross members. Each brace includes an upper portion, a lower portion, and a hinge assembly between the upper and lower portion including at least two intermediate links configured to allow translation of the lower portion relative to the upper portion. A force differential actuator subsystem is connected to each brace assembly. A plane defined by the medial hinge assembly and a plane defined by the lateral hinge assembly are angled as the joint approaches full extension.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 5 is a schematic side view showing one example of a hinge assembly for the brace of FIG. 4;

FIG. 6 is a schematic view depicting how the brace hinge assembly of FIG. 5 has two intermediate links and two non-actuated DOFs;

FIGS. 7A-7C are a schematic view of another hinge assembly design with only one intermediate link;

FIGS. 18-20D show schematic views of a brace capable of bi-directional torque;

FIGS. 21-23C are schematic views showing another version of a brace in accordance with the invention wherein FIG. 21 is a perspective front view and FIGS. 22 and 23C are partial cut-away side views;

DETAILED DESCRIPTION OF THE INVENTION

Figure 1:
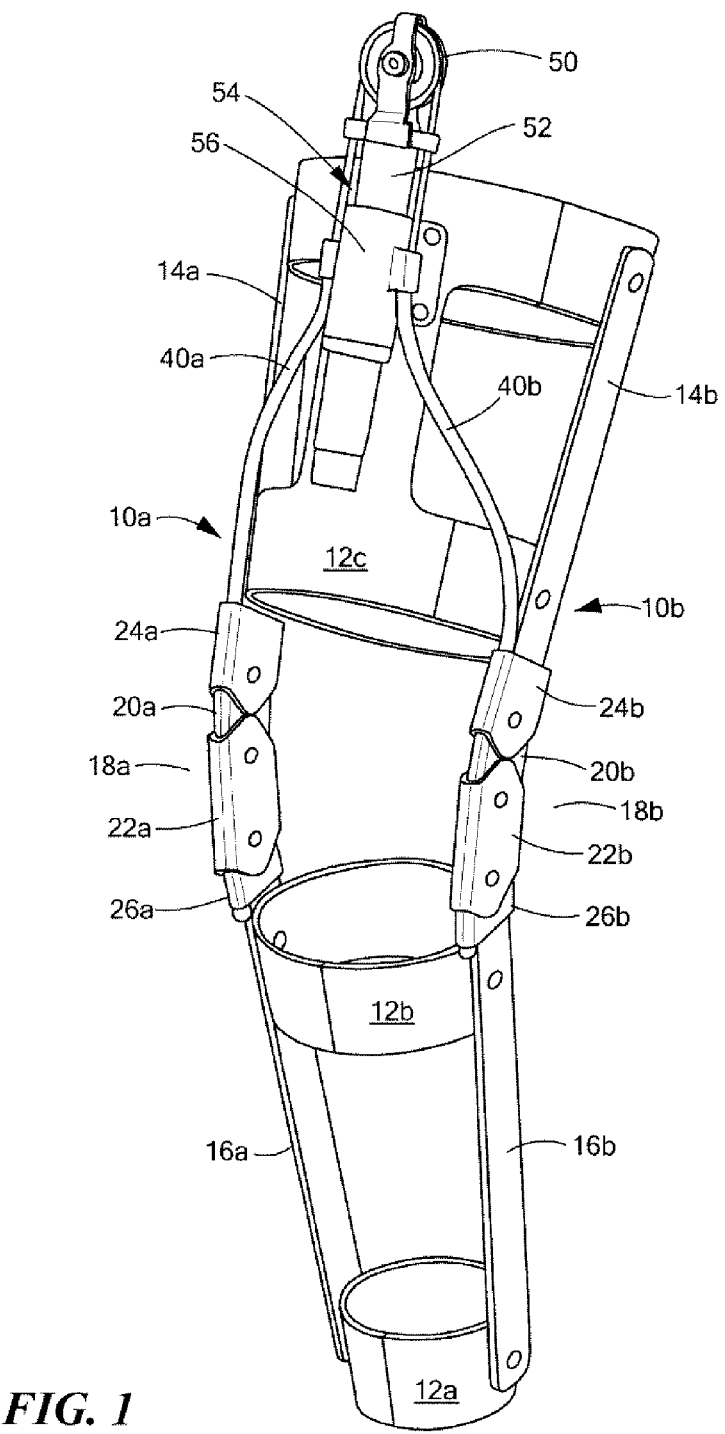
FIG. 1 is a schematic three dimensional front view showing an example of a knee brace system design with a force differential actuator subsystem in accordance with one example of the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 12:
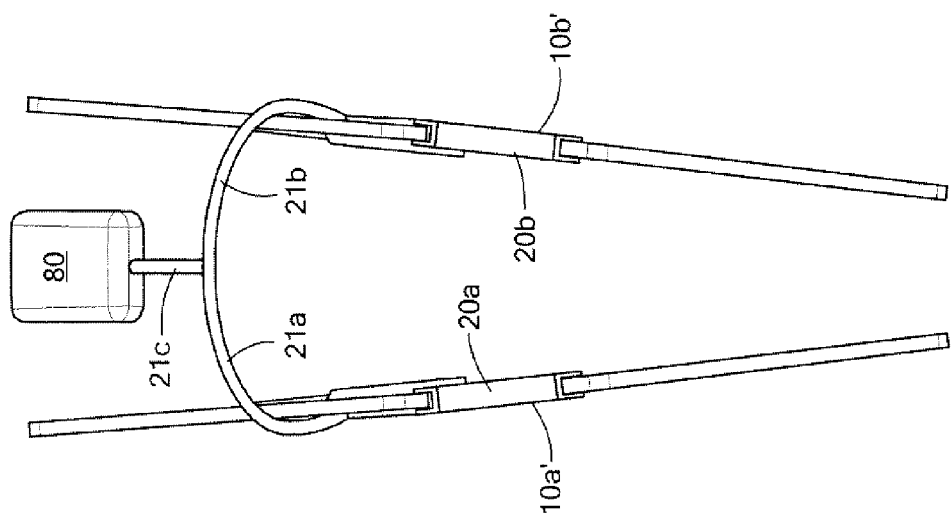

FIGS. 1-6 show one example of a brace system with medial brace 10a and lateral brace 10b. In some examples, there is only one brace but here braces 10a and 10b are securable about a leg, for example, via cross members 12a, 12b, and 12c (fabric with Velcro or other fasteners, plastic sleeve type configurations, or the like). Preferred is pliable material for all the cross members (e.g., fabric) so the medial and lateral braces can taper inwardly as shown in FIG. 12, for example, to better follow the contours of the knee or other joint.

Each brace includes upper portion 14 and lower portion 16 with a hinge assembly 18 therebetween. The design of the hinge may vary but here there are two intermediate links 20 and 22. The distal end of upper arm 14 includes end coupling 24 pivotably coupled to intermediate link 20 itself pivotably coupled in series to intermediate link 22 which is pivotably coupled to the proximal end coupling 26 of lower arm 16. Each link may support one or more pulleys (or sections thereof) as shown in FIG. 5 where wheel 30a is rotatably connected to links 24a and 20a, wheel 32a is rotatably connected to links 20a and 22a, and wheel 34a is rotatably connected to links 22a and 34a.

In other designs, the pulley wheels (or sections thereof) do not rotate. The pulley wheels can also be configured more like sprocket style designs, and the like. As shown in FIG. 6, the hinge assembly is configured with at least one non-actuated degree of freedom in addition to flexion and extension allowing translation of the lower brace portion 16 with respect to the upper brace portion 14.

Figure 2:
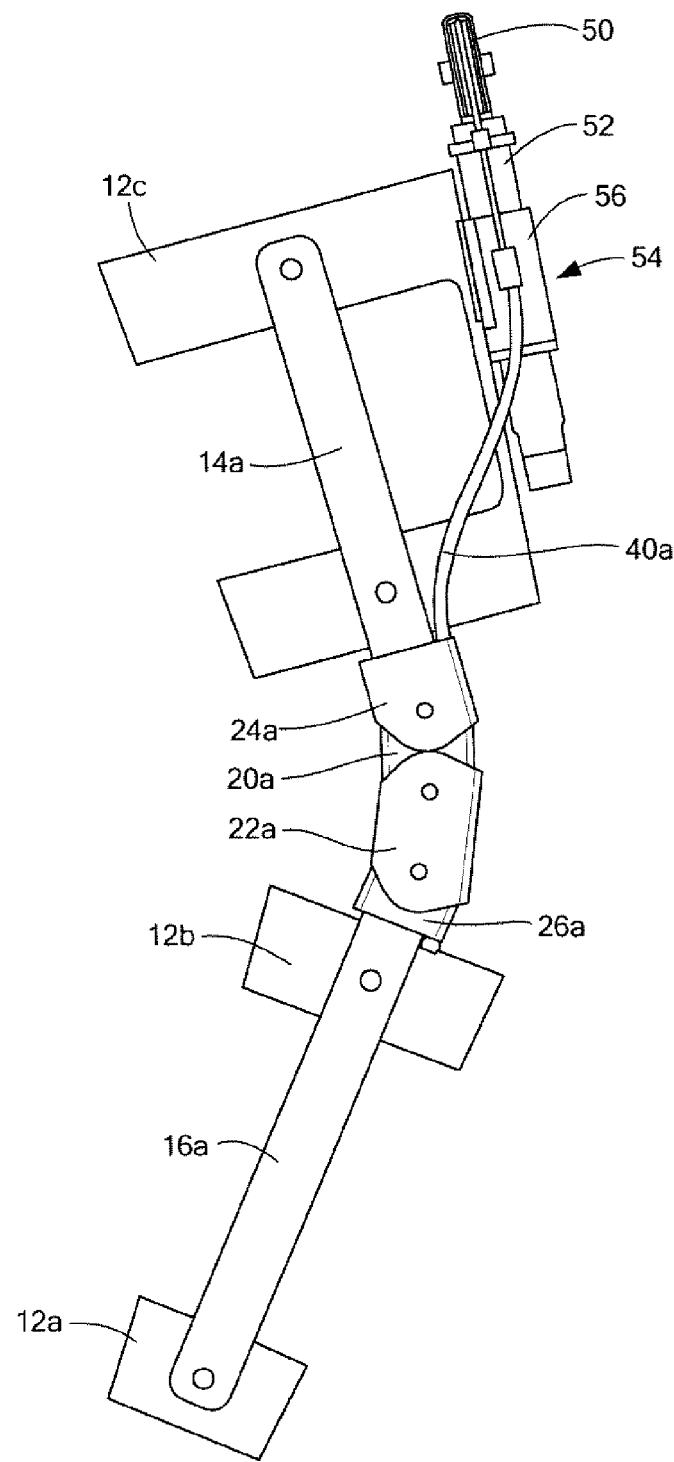
FIG. 2 is a schematic side view of the brace shown in FIG. 1.
Figure 3:
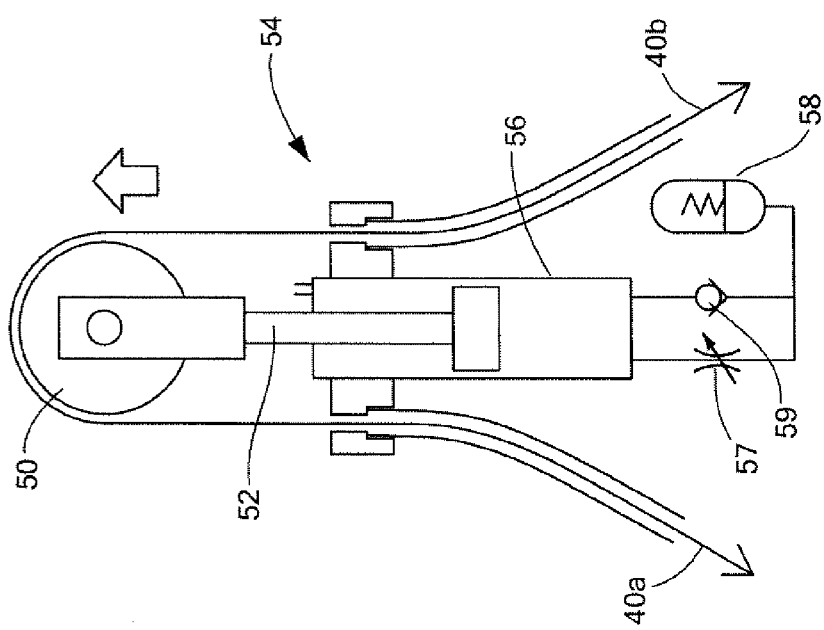
FIG. 3 is a schematic view of a force differential actuator subsystem in accordance with examples of the invention.

A force differential actuator subsystem, in this example, is connected to hinge assemblies 18a and 18b, FIGS. 1-3. In this particular example, the force differential actuator subsystem include interconnected tendons 40 (cables, cords, belts, bands, chains, and the like) over pulley wheels 30a, 32a, 34a, FIG. 5 and coupled at their distal ends to link 26 of lower arm 16 as shown at 42 in FIG. 5. The tendons continue over pulley 50, FIGS. 1-3 which equalizes the tension in cables 40a and 40b. Pulley 50 is rotatably coupled to piston 52 of hydraulic actuator 54 attached to cross member 12c, FIG. 1. Hydraulic fluid in cylinder 56 is forced into accumulator 58 when the braces bend with the knee (or other joint) as tendons 40a, 40b pull piston 52 down within cylinder 56. The top of cylinder 56 may be vented to atmosphere.

FIG. 3 also shows an example hydraulic circuit which would be useful for walking downhill or down stairs. In this case, flexion of the knee pulls on cables 40a and 40b causing piston 52 to push fluid through variable restriction 57 into a low-pressure accumulator 58. When extending the leg, fluid from the accumulator flows through check valve 59 and into cylinder 56, thus extending pulley 50 and taking up slack in cables 40a and 40b.

Figure 4:
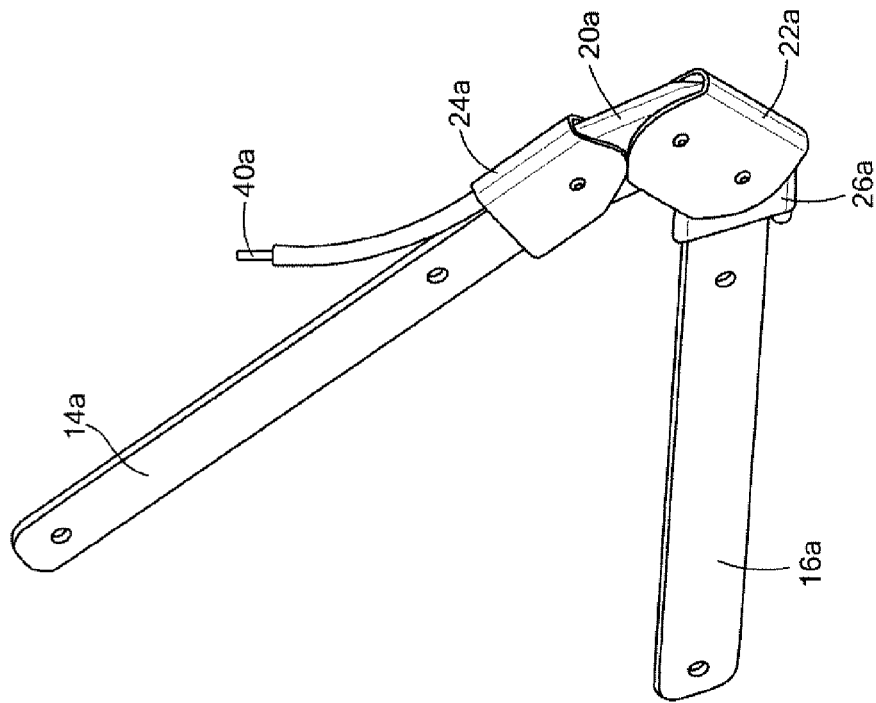
FIG. 4 is a schematic side view of one brace for the system shown in FIGS. 1 and 2.

FIG. 6 shows how the hinge assembly 18 of FIGS. 4-5 allows translation of the lower arm 16 in two degrees of freedom with respect to the upper arm 14a. The pulleys 30a, 32a and 34a, and intermediate links 20a and 22a form a parallel-motion mechanism which provides substantially parallel motion of the lower arm with respect to the upper arm without extending or retracting the cable. These two translational DOF are non-actuated, meaning that they can happen freely (except for friction) even when the cable is under load and the brace is exerting torques on the limbs adjacent to the joint. The two translational DOF make the brace far less sensitive to alignment with the body and avoid shear loading of the knee. "Pistoning" forces (along the long axes of the upper and lower arms) are also largely avoided, which minimizes the tendency of the brace to migrate, e.g. shift down the leg while walking.

In other designs, the force differential actuator subsystem may include an actuator for each brace with both actuators coupled by a differential hydraulic circuit.

Figure 9:
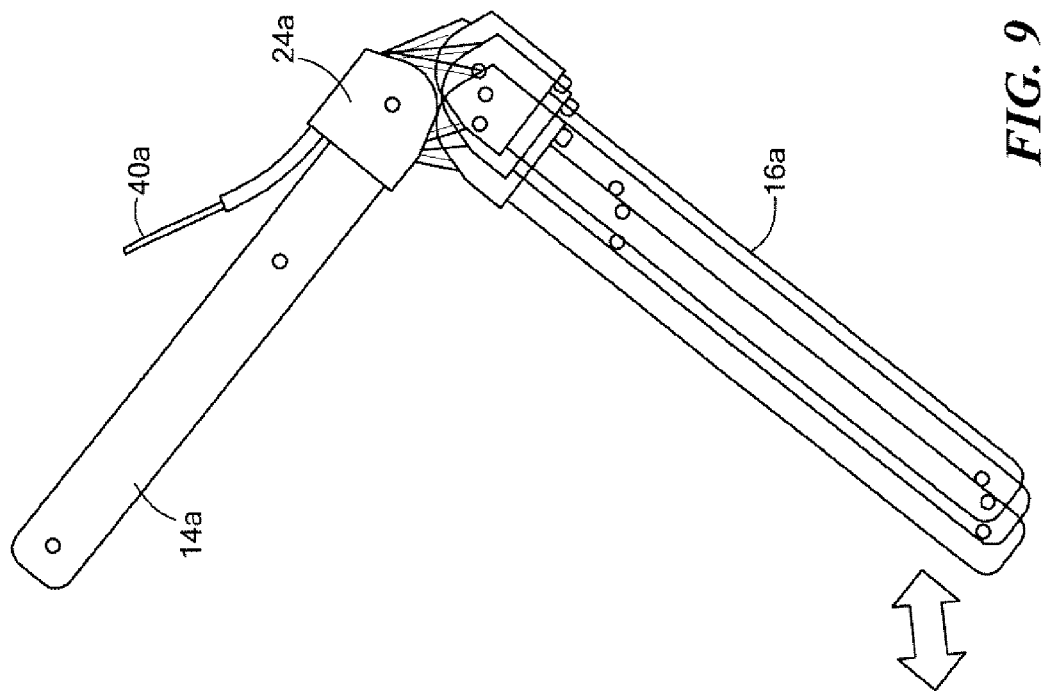
FIG. 9 is a depiction of the brace of FIGS. 7-8 showing how a hinge assembly with only one intermediate link exhibits a non-actuated degree of freedom in addition to flexion and extension allowing translation of the lower arm brace portion with respect to the upper arm brace portion.
Figure 8:
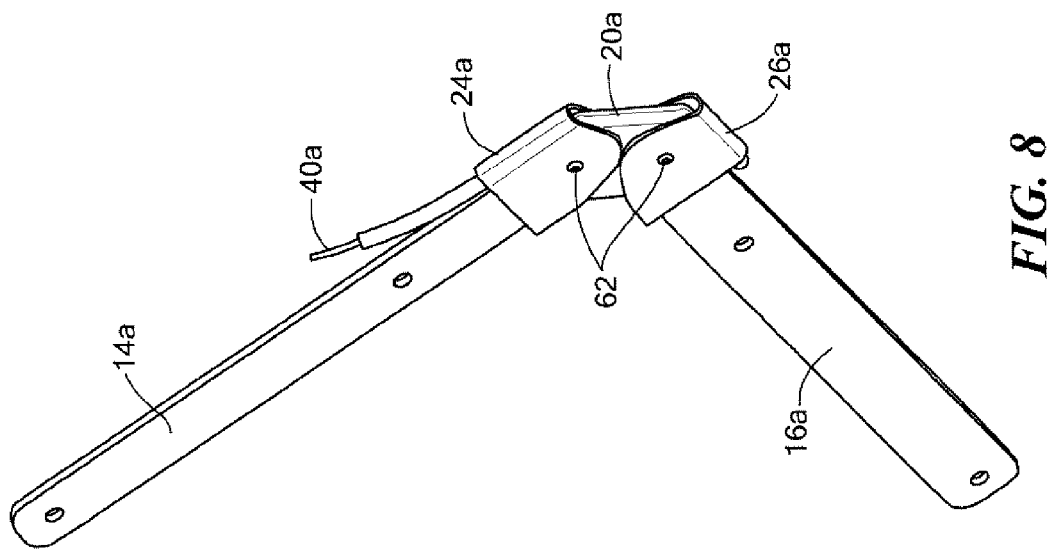
FIG. 8 is a schematic view showing the bending of the brace of the hinge assembly of FIG. 7.

FIGS. 7-9 show an example with only one intermediate link 20a. This version is potentially lighter and cheaper to manufacture than that of FIGS. 1, 2, 4-6. In FIGS. 7A-7C, pulling on cable 40a causes the brace to extend. As shown in FIG. 9, the hinge assembly also provides one non-actuated, translational parallel-motion DOF of the lower arm 16*a* relative to the upper arm 14*a*. In the knee brace example, this DOF mitigates vertical misalignment of the brace and minimizes shear loads on the knee, but is less effective for fore/aft misalignment and the resulting pistoning forces.

Figure 10:
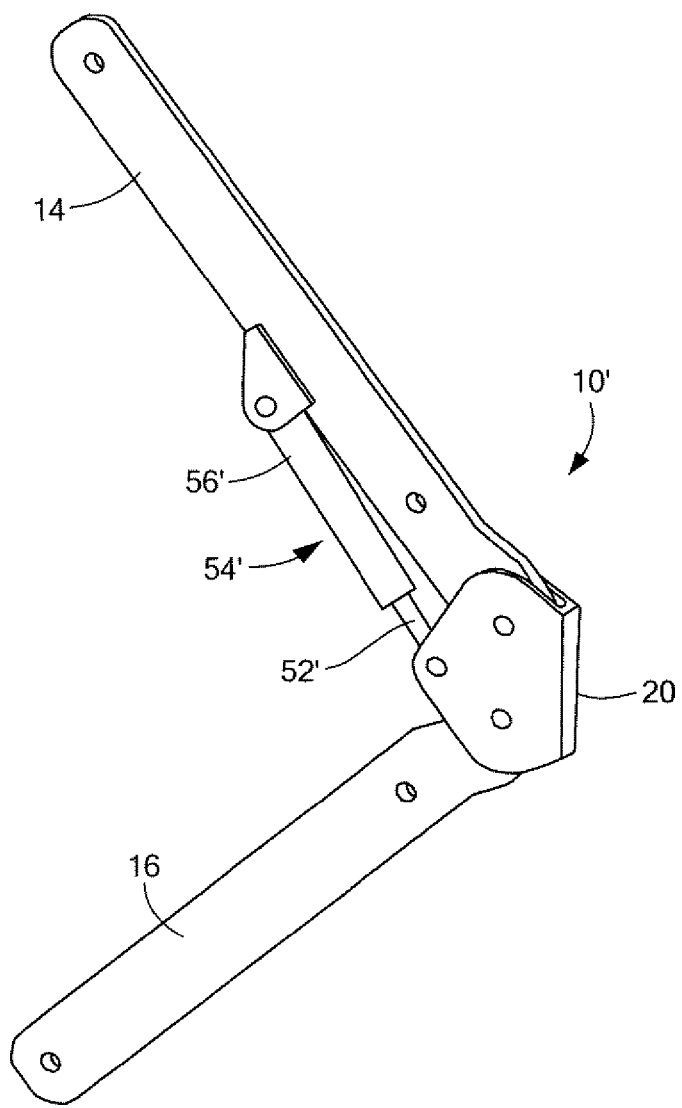
FIG. 10 is a schematic side view showing an example of another brace configuration in accordance with the invention.
Figure 11C:
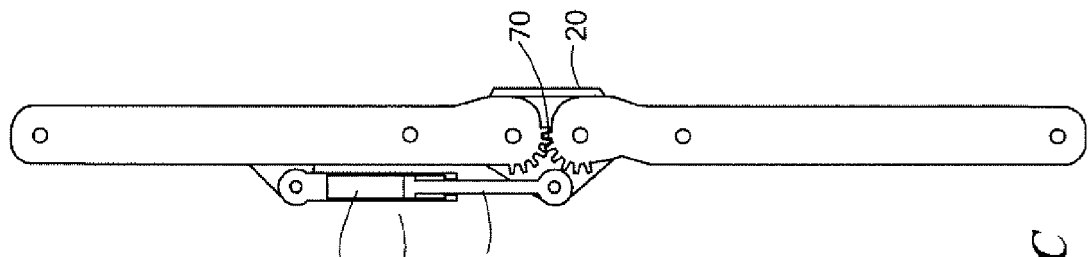
FIGS. 11A-11C are schematic cut-away views showing the operation of the brace depicted in FIG. 10.
Figure 11B:
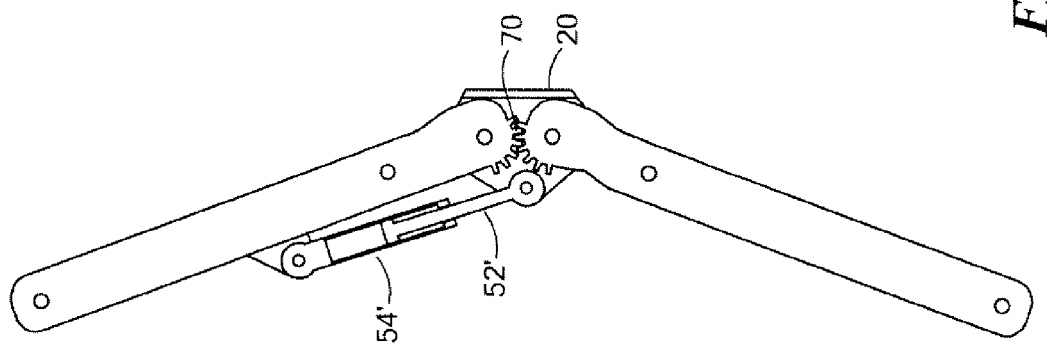
Figure 11A:
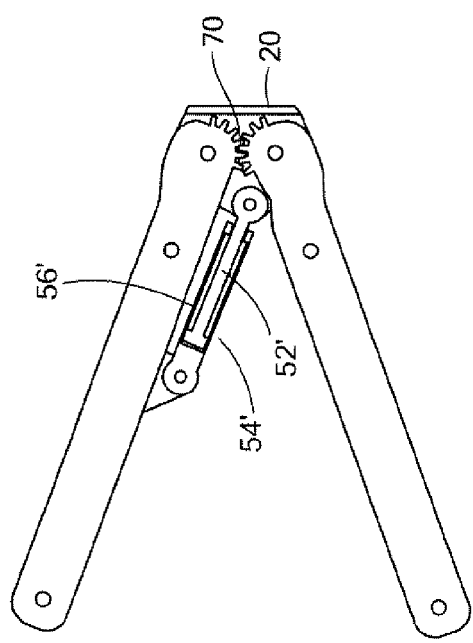
Figure 13:
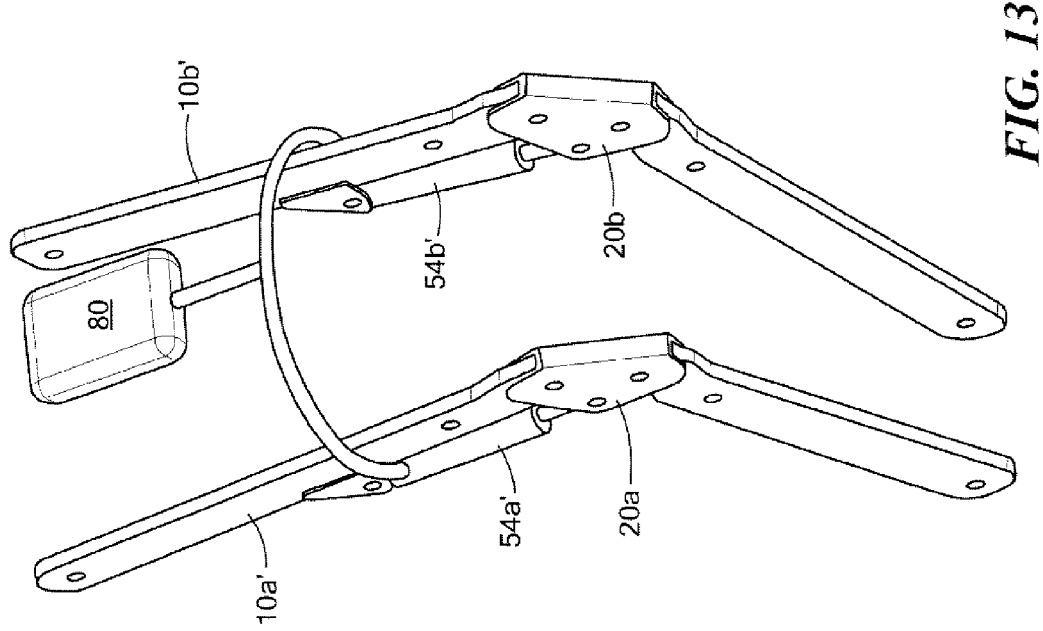
FIGS. 12 and 13 are schematic front views showing two braces as depicted in FIGS. 10 and 11 with their actuators coupled to a differential hydraulic circuit.

In another design, there is a kinematic coupling between the upper and lower portions. FIGS. 10-11, for example, show brace 10' with intermediate link 20 pivotably connected to upper arm 14 and lower arm 16 which both include meshing gear teeth as shown at 70. Each brace here includes actuator 54' with cylinder 56' pivotably connected to upper arm 14 and piston 52' pivotably connected to link 20. In this embodiment, as shown in FIGS. 12-13, the hydraulic actuators can be force-coupled by a differential hydraulic circuit, e.g. by conduits 12*a*, 21*b*, and 21*c* connecting to hydraulic control unit 80.

As shown in FIG. 12 (and FIG. 1), driving both brace assemblies removes the need for any rigid structures connecting between the medial and lateral braces. Soft fabric straps may be used. This reduces the size and weight of the brace and allows for width adjustment using straps. An additional advantage is that the hinge assemblies on the medial and lateral sides do not have to be parallel (as viewed from the front). They angle inwardly as defined by the plane of the drawing page. Since people's legs and knees are generally tapered, this allows the hinge assemblies to lie closer to the knee which reduces the likelihood of interference with the brace on the opposite leg. Each hinge assembly lies in an angled plane as the joint approaches full extension.

Figure 14:
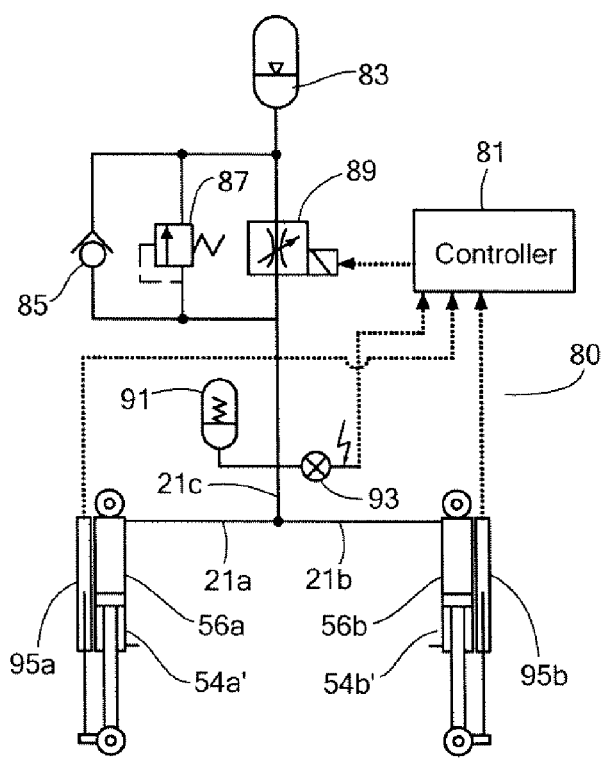
FIG. 14 is a schematic view showing one example of a suitable differential hydraulic circuit useful in accordance with various versions of the invention.
Figure 15:
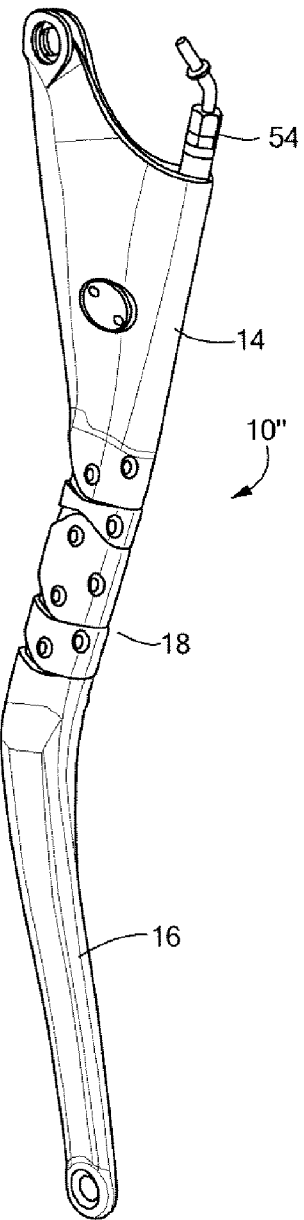
FIGS. 15-17 are schematic views showing an example of another brace in accordance with the invention with three intermediate links driven by a toothed belt and pulley sections.
Figures 16, 17:
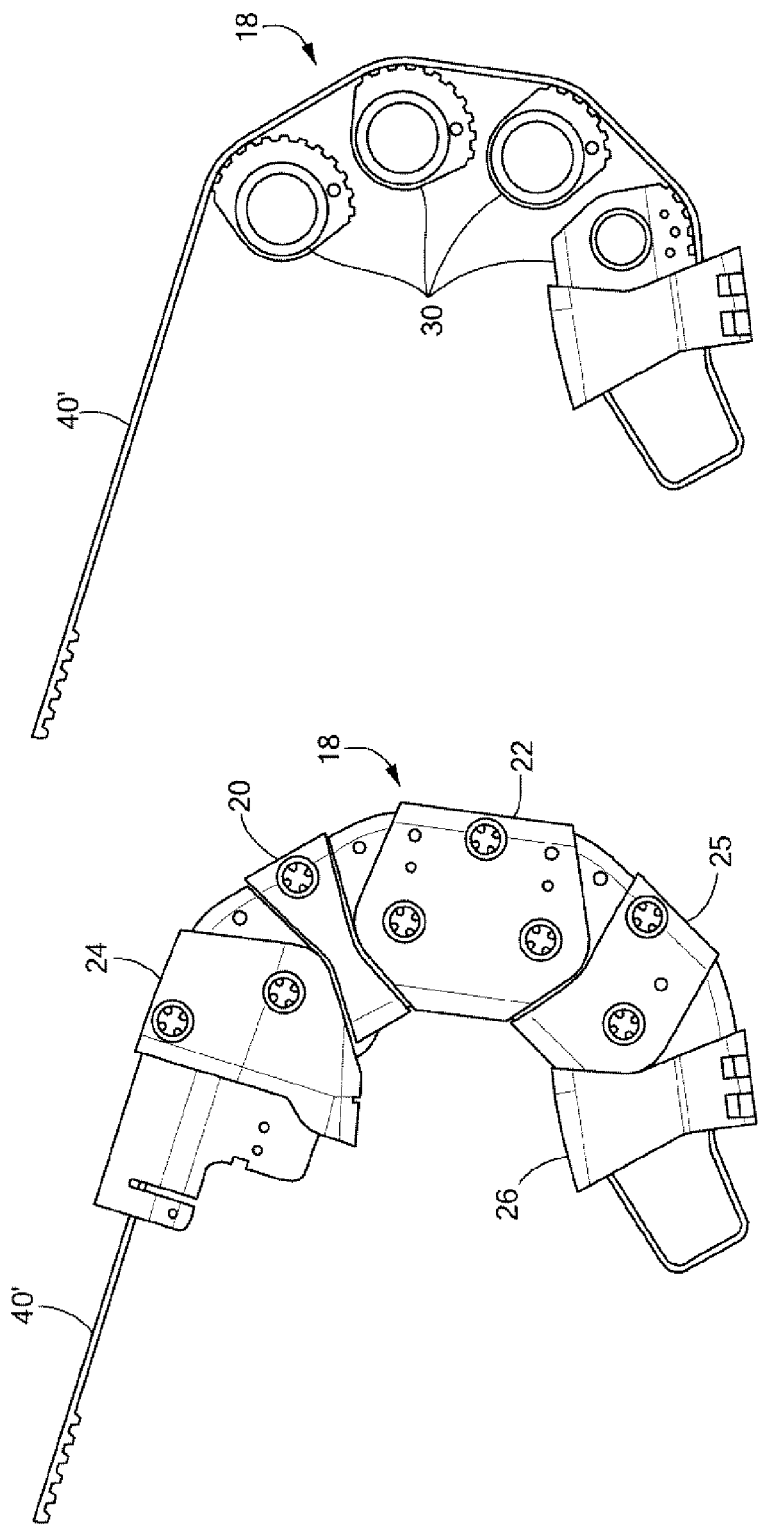
Figure 18:
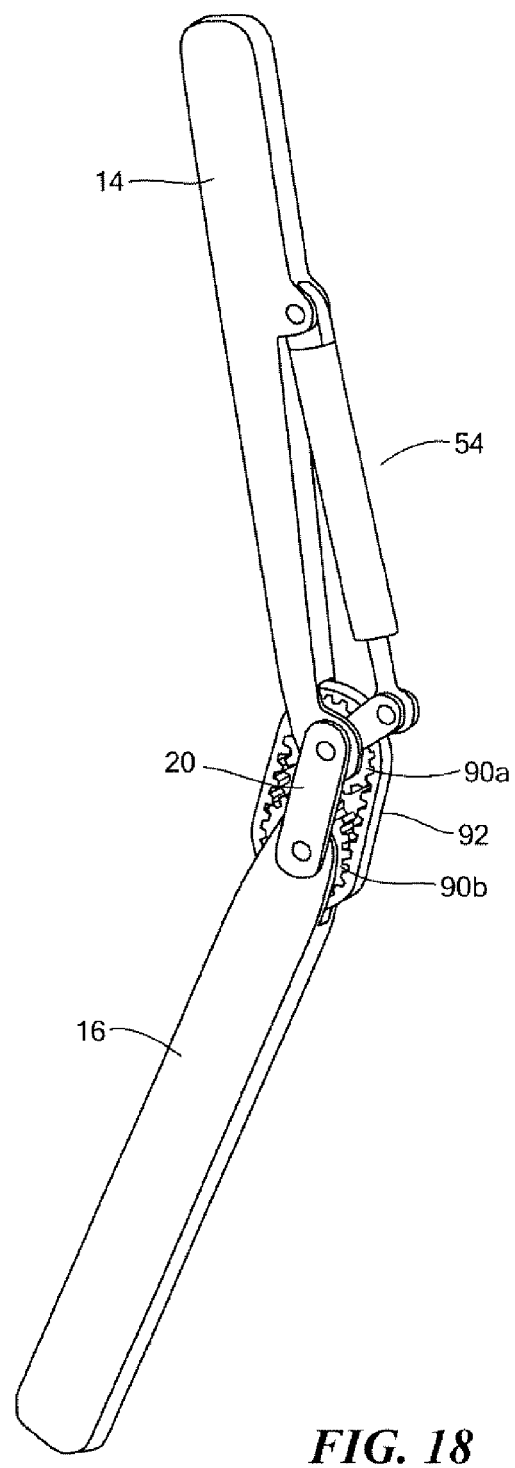
Figure 20D:
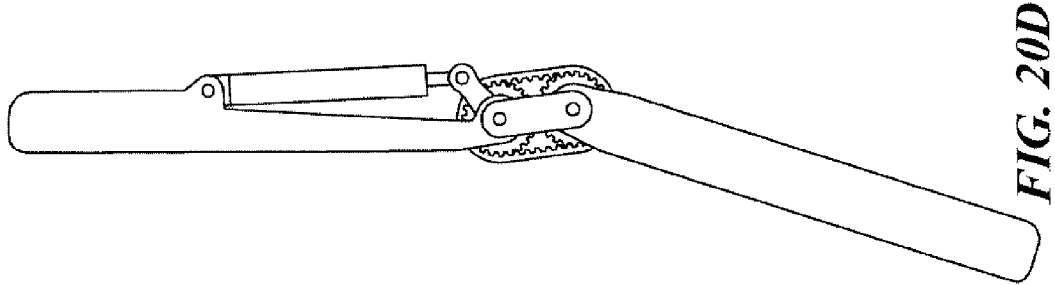
Figure 20C:
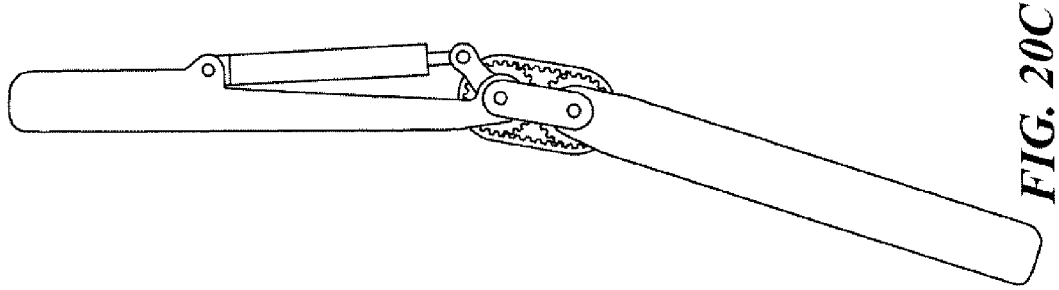
Figure 20B:
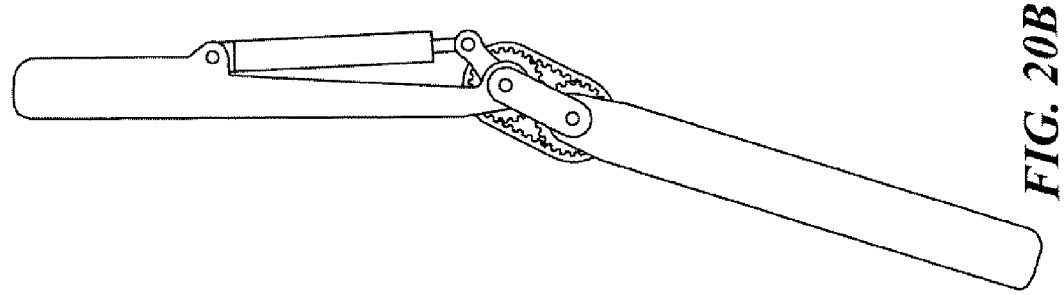
Figure 20A:
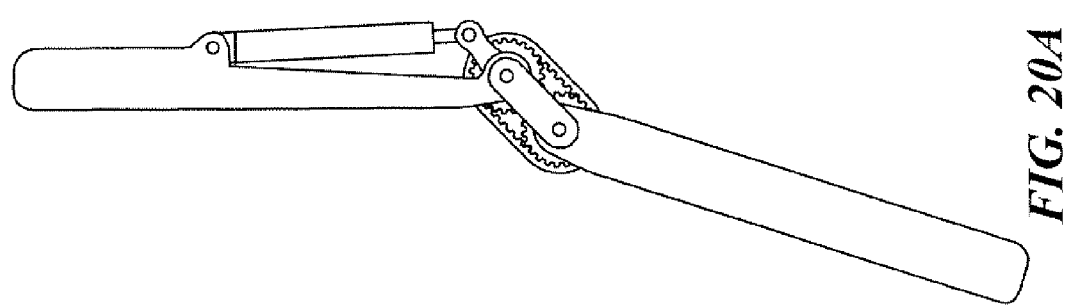

FIG. 14 shows an example of a hydraulic circuit intended to assist walking with a heavy pack. In this example, position sensors 95 and pressure sensor 93 provide knee position and torque data to controller 81 (e.g., a microprocessor, FPGA, microcontroller, or the like). Based on these inputs and knowledge of typical walking gait cycles, controller 81 is programmed to close valve 89 just prior to heel-strike. At heel-strike, the leg bends and forces fluid in cylinders 56 through conduits 21 and into spring accumulator 91. In effect, the brace acts like a spring during this phase of the gait cycle, called the "weight acceptance phase". The knee and brace flex, storing energy in the spring accumulator. Later in stance when the knee extends, pressurized fluid in the accumulator flows into cylinders 56 and assists the knee extensor muscles. If the knee extends further than its angle at heel-strike, pressure will drop below that of the low pressure accumulator 83 and fluid will flow through check valve 85 and into cylinders 56. This allows the knee to extend freely. Late in stance, knee extension velocity goes to zero (as the knee changes direction) and controller 81 is programmed to open valve 89 to allow free flow of fluid from cylinders 56 into the low pressure accumulator 83. This allows the leg to freely flex to provide ground clearance during the swing phase of the gait cycle. FIG. 14 also shows a pressure relief valve 87 which provides overload protection and assists the knee extensor muscles when stepping or jumping downward.

Other hydraulic circuits are possible and can be tailored for other behaviors, such as walking downhill, stair descent, etc. Circuits may also be designed to store energy on descent and use this energy for assisting ascent. Auxiliary power sources such as electric motors or fuel-driven engines can be used to enable sustained climbing, jumping etc. Other sensors such as foot force sensors, accelerometers, electromyography sensors, nerve implants, brain implants, etc. may be used as inputs to a controller which can modulate the force in actuators 54 thus modulating the torque applied by the brace to the wearer.

Other hinges assemblies are possible. FIGS. 15-19 show brace 10" with upper arm 14*a* and lower arm 16*a* and hinge assembly 18, tendon toothed belt 40' and actuator 54. With two such braces (e.g., medial and lateral), their actuators could be connected to a differential hydraulic circuit (see, e.g., FIG. 14) for force differential actuation, Intermediate links 20, 22, and 25 are pivotably connected in series and support pulley sections 30' with gear teeth thereon. To simplify FIGS. 16 and 17, only a short segment of teeth are shown, but the teeth in fact may extend into the hinge assembly and mate with the teeth of the pulley sections. The mating teeth prevent the pulleys from rotating more than necessary. This allows the back-side of the pulleys to be cut away, which makes the hinge assembly more compact. Functionally, this embodiment is the same as that of FIG. 5 except that there are three intermediate links. The hinge assembly is a parallel-motion linkage with two non-actuated DOFs. It allows the lower arm to freely translate in two DOFs as in FIG. 6.

FIGS. 18-20D, show an example of a tendon-style hinge assembly capable of bi-directional torque. In this example, the hinge assembly includes intermediate link 20 and pulleys (or sprockets) 90*a* and 90*b* banded by tendon 92 (e.g., a toothed belt or chain). Actuator 54 is pivotably coupled to gear 90*a*. FIG. 19 shows the actuated DOF. Extension or retraction of the actuator causes pulley 90*a* to rotate, which drives the lower arm 16 by means of tendon 92 and pulley 90*b* attached to or integral with the lower arm. Like the previous embodiments, the hinge assembly acts as a parallel-action mechanism. As shown in FIGS. 20A, 20B, 20C and 20D, the lower arm can translate freely in one DOF without requiring motion of the actuator. Other variations are possible. For instance, more intermediate links could be added, with each pair of adjacent pulleys (or sprockets) banded by a toothed belt or chain. In place of toothed pulleys and belts (or sprocket and chain), cable or cord could be used if prevented from sliding, e.g. by friction or by having cable segments attached to partial-rotation pulleys. The cable(s) could also make one or more wraps around the pulley(s). To allow a twisting DOF, actuator 54 could be connected to a differential hydraulic circuit in a brace system with two such braces (e.g., medial and lateral).

Figure 23C:
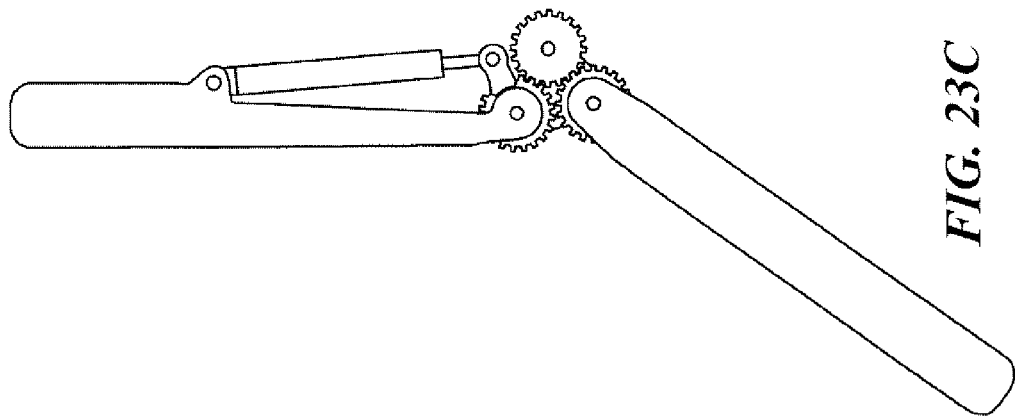
Figure 23B:
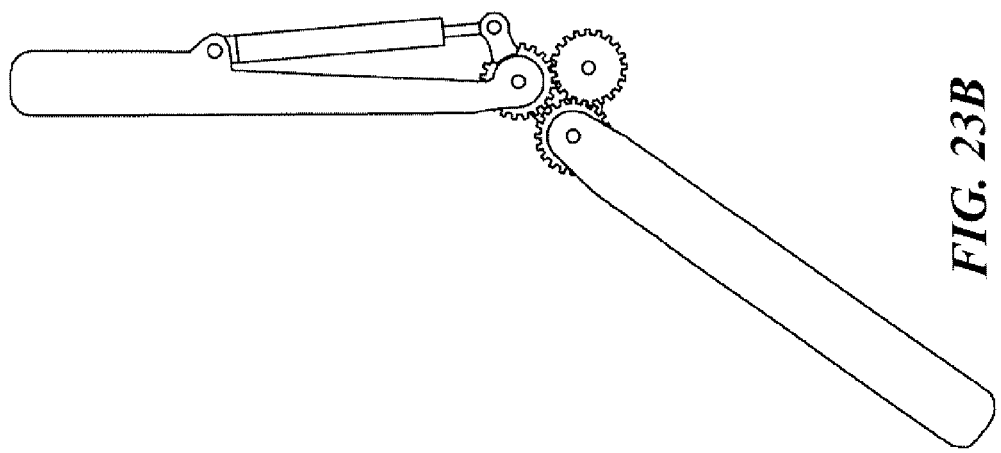
Figure 23A:
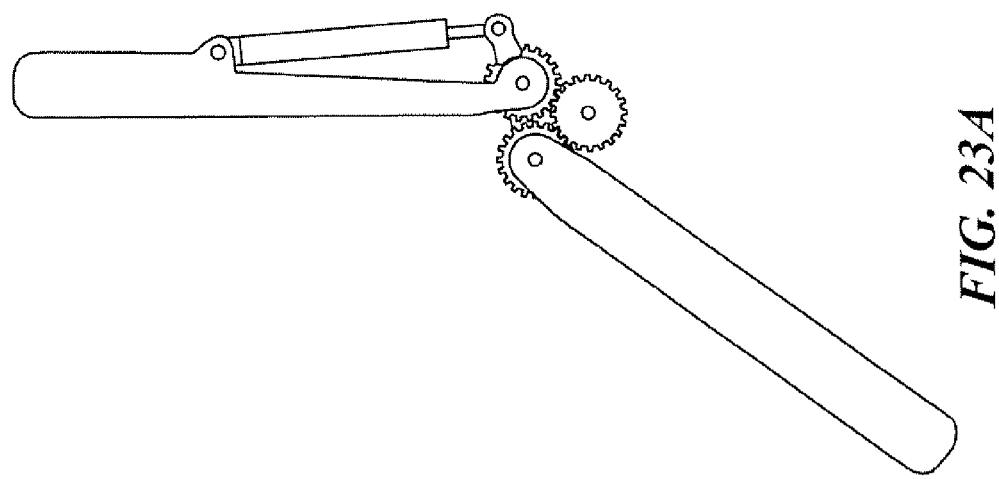
Figure 24:
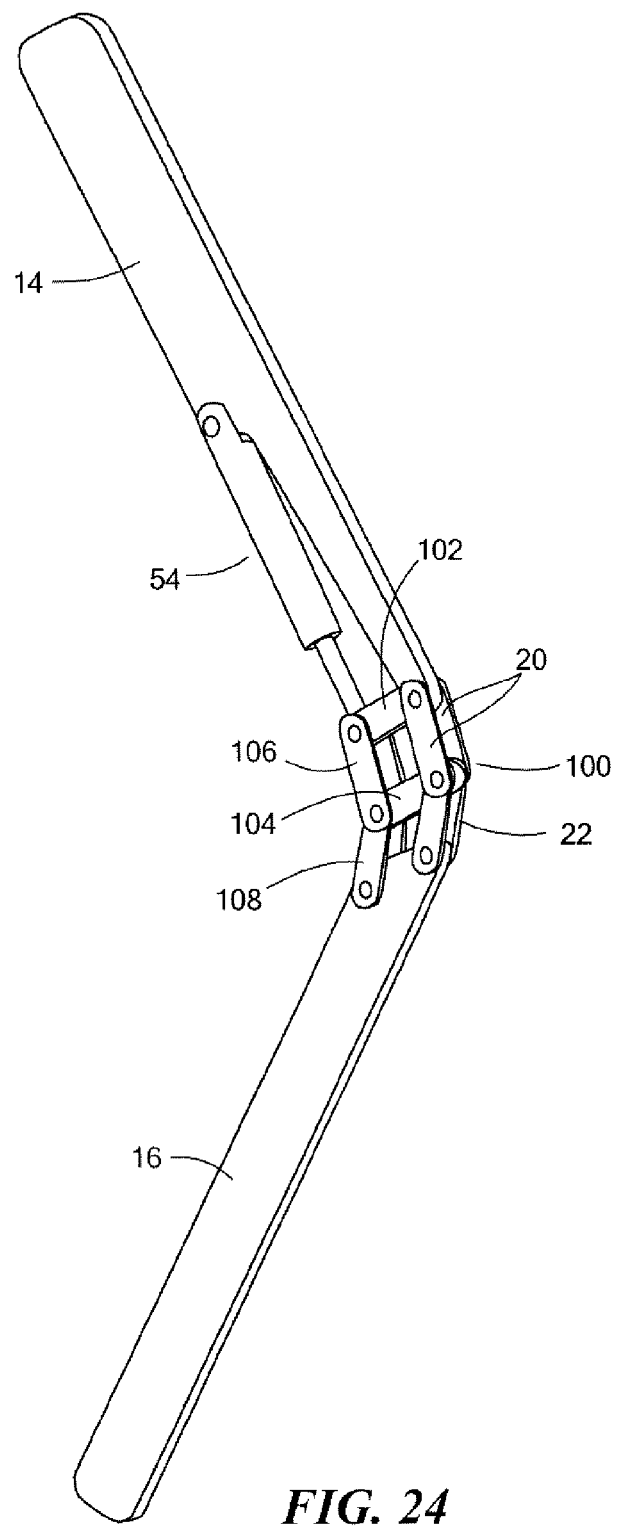
FIGS. 24-26D are schematic views showing examples of a brace hinge assembly including a parallel action mechanism in the form of a four bar linkage type configuration.

FIGS. 21-22 show an embodiment which is functionally very similar to that of FIGS. 18-20D, but where an intermediate gear 90*c* is used in place of toothed belt 92. In this example, gear 90*a* is rotatably connected to upper arm 14 and gear 90*b* is attached to lower arm 16. All three gears are rotatably attached to intermediate link 20. Gears 90*a* and 90*b* mesh with gear 90*c* but not with each other. FIG. 22 shows the actuated DOF and FIGS. 23A, 23B and 23C show the non-actuated DOF. As shown in FIGS. 23A-C, the hinge assembly acts as a parallel motion linkage to provide a translational DOF of lower arm 16 relative to upper arm 14.

Figures 25A, 25B, 25C:
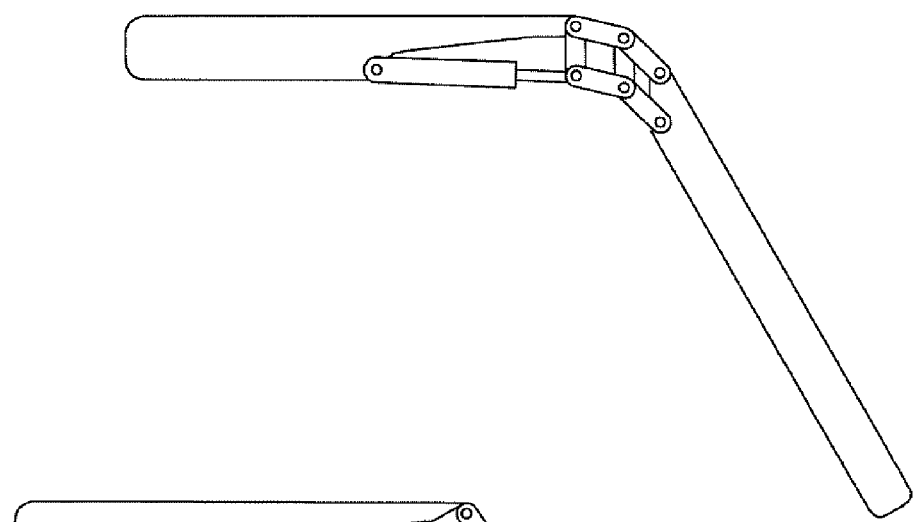
Figure 26B:
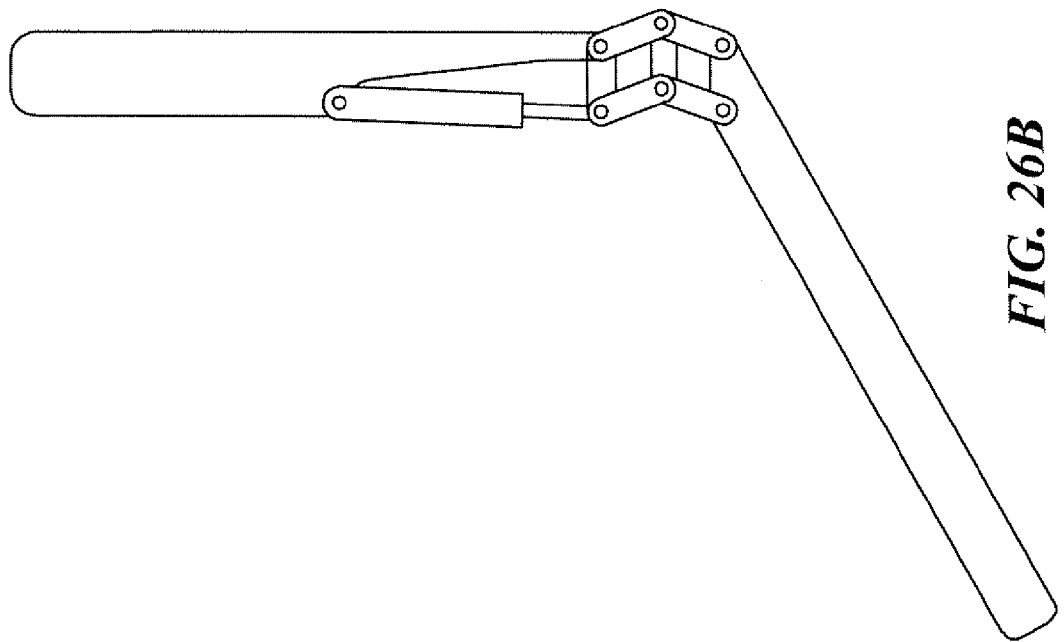
Figure 26A:
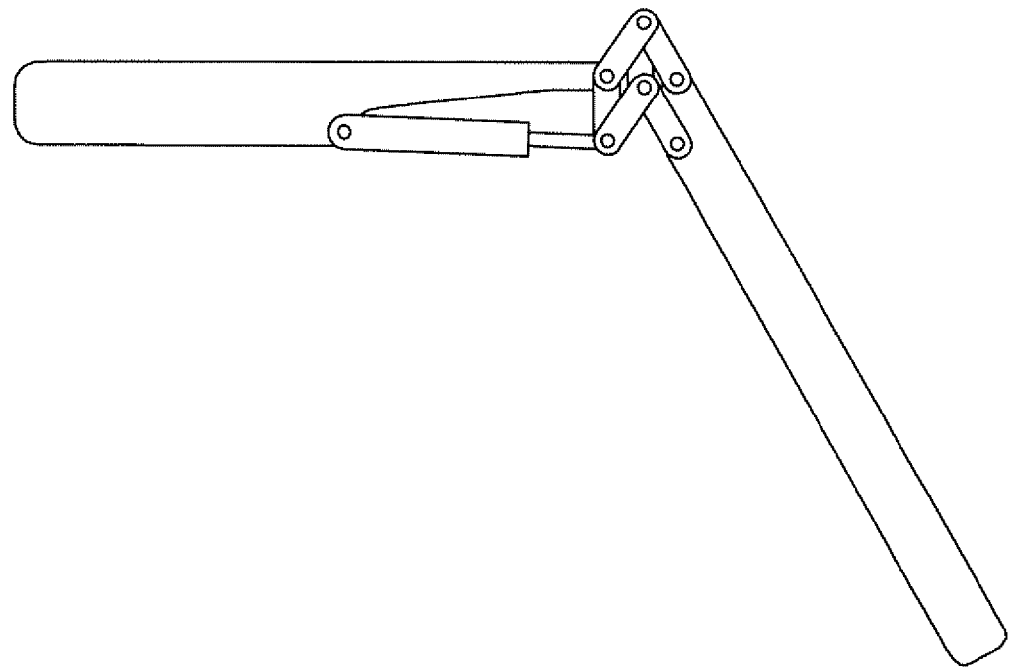
Figure 26D:
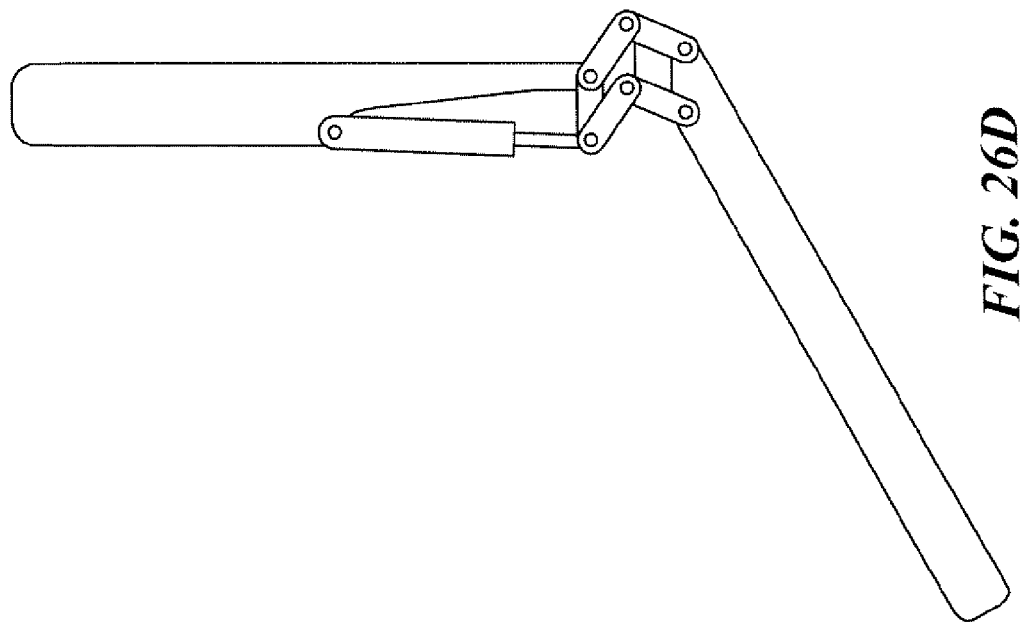
Figure 26C:
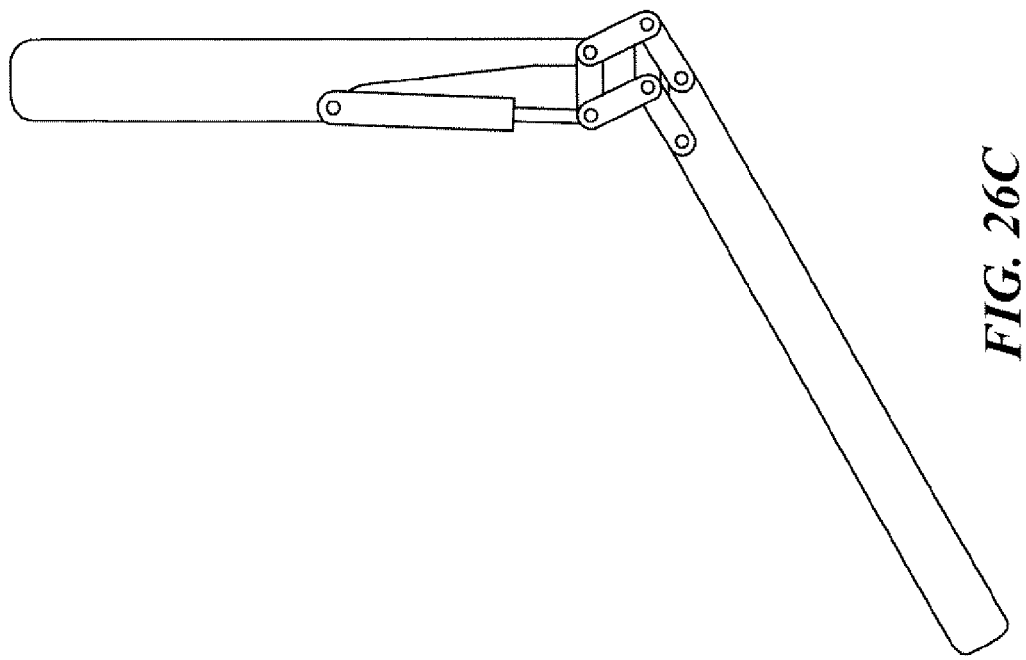

There are other ways to apply substantially equal and opposite torque to the upper brace arm and lower brace arm while allowing translation of the lower brace arm with respect to the upper brace arm. FIGS. 24-26D show an example that uses 4-bar parallelogram linkages instead of pulleys and tendons. In this example, the hinge assembly has two intermediate links 20 and 22 connected in series between upper arm 14 and lower arm 16. The hinge assembly also has offset links 102 and 104 which functionally take the place of pulleys, and drive links 106 and 108 which provide a similar function to the tendons of the previous examples. Unlike tendons, the drive links can operate in tension and compression, allowing bi-directional torque to be applied to the upper and lower arms. Actuator 54 is rotatably attached to the upper arm and to drive link 106. Other variations are possible, e.g. driving the offset link with a cam, tendon, rack, etc. Drive link 106 pushes or pulls on drive link 108, which applies torque to the lower arm 16. FIGS. 25A, 25B and 25C show the actuated DOF, and FIGS. 26A, 26B, 26C and 26D show the two non-actuated DOFs: vertical translation of the lower arm in FIGS. 26A-B and horizontal translation in FIGS. 26C-D.

Figure 27:
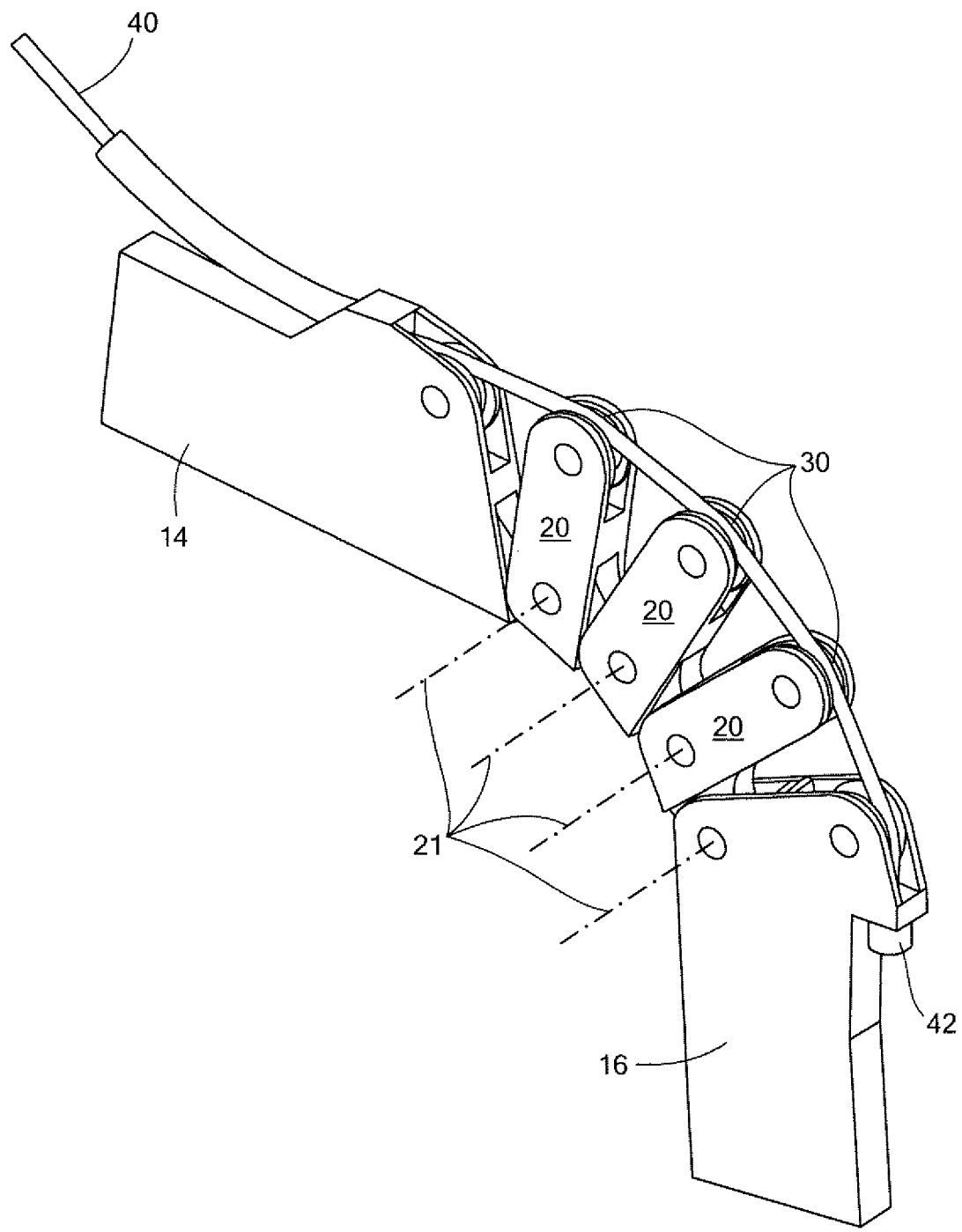
FIG. 27 is a schematic view showing another example of a brace hinge assembly with a tendon and pivotably connected intermediate links in series.

FIG. 27 shows another tendon hinge design with three intermediate links 20 each supporting a rotating or fixed pulley wheel (or section thereof) 30 offset from the pivot axes 21 of the links. The use of offset pulleys approximates the action of a larger pulley and provides a more compact and lighter design. Other variations are possible where there are two or more pulleys per link, or the pulleys can be non-rotating and the cable can slide. As shown, the hinge assembly 18 provides two substantially non-actuated translational DOFs of the lower arm 16 with respect to the upper arm 14. In this example, however, the parallel action mechanism is only approximate and there can be small translational forces applied by the brace to the wearer if the intermediate links do not fan out equally.

In general, it should be understood that the parallel action mechanisms described herein do not have to be perfect. Some deviation from parallel motion may even be desirable, e.g. to make the links of the hinge assembly open in a certain order, or to compensate for friction. As long as the hinge action produces approximately parallel motion of the lower arm with respect to the upper arm, the translational forces applied to the arms of the brace by the hinge assembly will be small, even when the brace is under load.

It is further understood that substantially free translation of a brace lower portion with respect to the brace upper portion means translation as generally depicted in FIG. 6, for example, when the brace is angled but not necessarily translation when the brace is straight or fully bent.

In accordance with the invention, a flexion or extension torque is applied to a joint (e.g., knee, ankle, finger joint, or the like) while allowing the normal motion of the joint. For instance, to assist the knee joint, a torque is applied to the thigh and an equal and opposite torque is applied to the foreleg. Properly applied, these torques cancel out and avoid shear forces on the joint.

In some designs, the knee brace allows twisting of the foreleg, is relatively insensitive to alignment, is lightweight, low-profile, and fits people (or animals) of various sizes. Some brace system designs include straps made of soft materials that can be integrated into clothing or worn under clothing.

Thus, although specific features of the invention are shown in some drawings and not in others, this is for convenience only as some features may be combined with other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A brace system comprising:
a medial brace and a lateral brace securable via cross members, each brace including:
an upper portion,
a lower portion, and
a hinge assembly between the upper and lower portion including a tendon and at least two intermediate links configured to allow translation of the lower portion relative to the upper portion; and
a force differential actuator subsystem connected to the medial brace and the lateral brace, and including at least one hydraulic actuator coupled to the tendons.

2. The brace system of claim 1 in which each hinge assembly includes a parallelogram linkage.

3. The brace system of claim 1 in which the force differential actuator subsystem includes, for each brace, respective hydraulic actuators coupled to a differential hydraulic circuit.

4. The brace system of claim 1 in which each hinge assembly includes at least sections of pulley wheels associated with the intermediate links, wherein the tendons run over the pulley wheel sections.

5. A brace system comprising:
a medial brace and a lateral brace securable via cross members, each brace including:
an upper portion,
a lower portion, and
a hinge assembly between the upper and lower portions including a mechanical parallel action mechanism with at least one intermediate link; and
a force differential actuator subsystem connected to the hinge assemblies, including a tendon for each hinge assembly and at least one actuator.

6. The brace system of claim 5 in which the cross members are pliable.

7. The brace system of claim 5 in which upper and lower portions of each brace are pivotably connected by two or more intermediate serial links in the hinge assembly.

8. The brace system of claim 5 in which each hinge assembly is configured with at least one non-actuated degree of freedom allowing translation of the lower portion with respect to the upper portion.

9. The brace system of claim 5 in which the tendons for each hinge assembly are interconnected and differentially coupled to the at least one actuator.

10. The brace system of claim 5 in which the force differential actuator subsystem includes, for each brace, a respective actuator coupled to a differential hydraulic circuit.

11. The brace system of claim 5 in which each hinge assembly includes a plurality of serially connected pivoting links, wherein at least some of the links are coupled together by at least a pulley wheel section rotatably coupled between adjacent links.

12. A brace system comprising:
a medial brace and a lateral brace securable via cross members, each brace including:
an upper portion;
a lower portion; and
a mechanical parallel action hinge assembly pivotably coupling the upper and lower portions including at least one intermediate link; and
an actuator subsystem connected to the hinge assemblies, including a tendon and at least one actuator, and configured to apply substantially equal and opposite torque to the upper portions and lower portions while allowing substantially free translation of the lower portions with respect to the upper portions.

13. The brace system of claim 12 in which the mechanical parallel action hinge assemblies each include at least sections of pulley wheels associated with the intermediate links, wherein the tendon runs over the pulley wheel sections.

14. The brace system of claim 12 in which the mechanical parallel action hinge assemblies each include a four bar linkage with at least one link driven by the at least one actuator.

15. The brace system of claim 12 in which the mechanical parallel action hinge assemblies each include gears associated with their respective intermediate links, wherein the intermediate links or at least one of the gears is driven by act the at least one actuator.

16. The brace system of claim 12 wherein the mechanical parallel action hinge assemblies each have at least two serially connected intermediate links.

17. A brace system comprising:
a medial brace and a lateral brace securable via cross members, each brace including:
an upper portion;
a lower portion; and
a hinge assembly pivotably coupling the upper and lower portions and including at least two serially connected intermediate links; and
a torque actuator subsystem connected to the hinge assemblies, including a tendon and at least one actuator, and configured to apply substantially equal and opposite torque to the upper portions and lower portions while allowing substantially free translation of the lower portions in two planar degrees of freedom with respect to the upper portions.

18. The brace system of claim 17 in which the hinge assemblies each include at least sections of pulley wheels associated with their respective intermediate links, wherein the tendon runs over the pulley wheel sections.

19. The brace system of claim 17 in which the hinge assemblies each include a four bar linkage with at least one link driven by the at least one actuator.

20. The brace system of claim 17 in which the hinge assemblies include gears associated with the intermediate links, wherein at least one of the gears is driven by the at least one actuator.

21. A brace system for a joint comprising:
a medial brace and a lateral brace securable via flexible cross members, each brace including:
an upper portion,
a lower portion, and
a hinge assembly between the upper and lower portion including a tendon and at least two intermediate links configured to allow translation of the lower portion relative to the upper portion; and
a force differential actuator subsystem connected to the medial brace and the lateral brace, including at least one hydraulic actuator coupled to the tendons, wherein a first plane is defined by the medial hinge assembly and a second plane is defined by the lateral hinge assembly, wherein the first and second planes are angled nonparallel to each other as the joint approaches full extension.

22. The brace system of claim 21 in which each hinge assembly includes a parallelogram linkage.

23. The brace system of claim 21 in which the force differential actuator subsystem includes, for each brace, respective hydraulic actuators coupled to a differential hydraulic circuit.

* * * * *